United States Patent
Nestler et al.

(10) Patent No.: US 7,253,311 B2
(45) Date of Patent: Aug. 7, 2007

(54) METHOD FOR THE PRODUCTION OF ACRYLIC ACID BY HETEROGENEOUSLY-CATALYSED GAS-PHASE OXIDATION

(75) Inventors: Gerhard Nestler, Vienna (AT); Juergen Schroeder, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 258 days.

(21) Appl. No.: 10/490,104

(22) PCT Filed: Sep. 30, 2002

(86) PCT No.: PCT/EP02/10952

§ 371 (c)(1),
(2), (4) Date: Mar. 25, 2004

(87) PCT Pub. No.: WO03/029177

PCT Pub. Date: Apr. 10, 2003

(65) Prior Publication Data

US 2004/0260121 A1    Dec. 23, 2004

(30) Foreign Application Priority Data

Oct. 1, 2001 (DE) ................................ 101 48 566

(51) Int. Cl.
*C07C 51/16* (2006.01)
(52) U.S. Cl. ........................ 562/545; 562/546; 562/547
(58) Field of Classification Search ................ 562/523, 562/544, 546, 547
See application file for complete search history.

(56) References Cited

U.S. PATENT DOCUMENTS

| | | | | |
|---|---|---|---|---|
| 3,846,336 A | * | 11/1974 | Levy | 502/211 |
| 4,031,135 A | | 6/1977 | Engelbach et al. | |
| 4,147,885 A | | 4/1979 | Shimizu et al. | |
| 6,069,271 A | * | 5/2000 | Tanimoto et al. | 562/545 |
| 6,525,217 B1 | * | 2/2003 | Unverricht et al. | 562/544 |

FOREIGN PATENT DOCUMENTS

| | | | |
|---|---|---|---|
| DE | 23 11 883 | | 9/1973 |
| DE | 199 55 176 | | 1/2001 |
| DE | 19955176 | * | 1/2001 |
| EP | 0 253 409 | | 1/1988 |
| EP | 0 575 897 | | 12/1993 |
| EP | 0 911 313 | | 4/1999 |
| JP | 2000-053611 | | 2/2000 |
| JP | 2000-169420 | | 6/2000 |

* cited by examiner

*Primary Examiner*—Karl Puttlitz
(74) *Attorney, Agent, or Firm*—Oblon, Spivak, McClelland, Maier & Neustadt, P.C.

(57) ABSTRACT

Acrylic acid is prepared from propene by means of gas-phase oxidation by a process in which a starting gas mixture which contains propene and steam and whose molar propene/steam ratio is $\geq 1$ and whose propane content is $\leq 5\%$ is passed at elevated temperatures through a fixed catalyst bed comprising successive catalyst part-beds A and B, the part-bed A passed through first containing, as active material, a mixed oxide containing the elements Mo, Bi and Fe and the part-bed B containing, as active material, a mixed oxide containing the elements Mo and V, in a manner such that at least 96.5 mol % of propene are converted in a single pass through part-bed A.

8 Claims, No Drawings

METHOD FOR THE PRODUCTION OF ACRYLIC ACID BY HETEROGENEOUSLY-CATALYSED GAS-PHASE OXIDATION

The present invention relates to a process for the preparation of acrylic acid from propene by means of gas-phase oxidation, in which a starting gas mixture which contains propene and steam and whose molar propene/steam ratio is $\geq 1$ and whose propane content is $\leq 5\%$ is passed at elevated temperatures through a fixed catalyst bed comprising successive catalyst part-beds A and B, the part-bed A passed through first containing, as active material, a mixed oxide containing the elements Mo, Bi and Fe and the part-bed B containing, as active material, a mixed oxide containing the elements Mo and V. The present invention furthermore relates to the use of the acrylic acid obtained by this process.

Acrylic acid and the esters prepared from it are important starting materials in the preparation of polymers which are used, for example, as superabsorbers, adhesives, surface coating resins or coating dispersions.

The acrylic acid isolated after a gas-phase oxidation is, however, contaminated with carboxylic acid, such as acetic acid, propionic acid and diacrylic acid, allyl acrylate, carbonyl compounds and polymerization inhibitors. Since these byproducts are generally undesired, they have to be separated off in expensive purification operations, as a rule by distillation.

Owing to the similarity of acrylic acid to the byproducts formed in the gas-phase oxidation with respect to the chemical and physical properties, such as boiling point and molecular weight, separating off of the byproducts, in particular the carboxylic acids and allyl acrylate, is virtually impossible. The number of theoretical plates required for a fractional distillation results in the acrylic acid being subjected to thermal stress for a relatively long time and, as a consequence of this, in polymer formation on column trays, pipes, pumps and valves. In particular, the separation of propionic acid from the acrylic acid by distillation is not possible at all on an industrial scale. The same applies to the separation of the propionates from the corresponding acrylates.

If the acrylic acid or its esters is or are polymerized, the carboxylic acids are low molecular weight impurities which, unless the dispersions were to be deodorized by an expensive procedure, would slowly evaporate from the polymers.

No less undesirable is allyl acrylate as a byproduct, since it has a destabilizing effect on acrylic acid and, particularly as a crosslinking agent in the polymerization, decisively influences the polymer property. Expensive purification operations are the result.

In view of these problems, various approaches were adopted for reducing the propionic acid content by modifying the catalyst.

JP-A-2000-53611 proposes a thermal aftertreatment of the acrylic acid-containing oxidation gas mixture at 300-500° C. in the presence of oxides of the elements Mo, Fe, Co and/or Ni. Although this aftertreatment reduces the propionic acid content, it leads to acrylic acid losses of 8%.

DE-A-23 11 883 postulates that propene not converted in the 1st oxidation stage is oxidized to propionic acid in the 2nd stage. According to this publication, the amount of propionic acid can be reduced to 550 ppm in the case of an Mo/V mixed oxide catalyst with the addition of a small amount of alkali metal for the 2nd oxidation stage.

According to JP-A 2000-169420, propionic acid is also formed starting from acrolein and acrylic acid. According to this publication, the propionic acid content is reduced by choosing an Mo/V/Sb/Pb mixed oxide catalyst in the 2nd oxidation stage.

These publications apply to starting gas mixtures having a substantially higher steam content than propene content. A high steam content has an advantageous effect on the acrylic acid selectivity of the oxidation reaction, as described in U.S. Pat. No. 4,147,885.

Very generally, the prior art indicates that it is important to dilute the propene with steam or other inert gases.

U.S. Pat. No. 4,031,135 describes the recycling of the uncondensable gases at the end of the oxidation to the starting gas mixture, which increasingly effects acrylic acid selectivity. However, the maximum propene conversion is 95 mol %. Furthermore, no information is given concerning the byproducts.

According to EP-A-0 253 409, it is advantageous to replace the steam with nonaqueous diluent gases, such as propane. Here, a heat capacity of $\geq 6.5$ cal/g mol (° C.) for the recycled gases is important. According to this publication, the acetaldehyde and/or acetic acid content is reduced. However, the use of propane as a diluent gas inevitably leads to a higher propionic acid content as byproduct. Low steam contents give advantageous acetic acid values only in combination with propene conversions of <96 mol %. The effect of the reaction conditions on the propionic acid is not indicated in any of these publications.

It is an object of the present invention to provide a process for the preparation of acrylic acid by catalytic gas-phase oxidation of propene, which process gives an acrylic acid having a very low allyl acrylate and propionic acid content. In particular, it is intended to obtain an acrylic acid which contains less than 400 ppm of propionic acid and less than 100 ppm of allyl acrylate without additional aftertreatment steps.

We have found that this object is achieved by a process for the preparation of acrylic acid from propene by means of gas-phase oxidation, in which a starting gas mixture which contains propene and steam and whose molar propene/steam ratio is $\geq 1$ and whose propane content is $\leq 5\%$ is passed at elevated temperatures through a fixed catalyst bed comprising successive catalyst part-beds A and B, the part-bed A passed through first containing, as active material, a mixed oxide containing the elements Mo, Bi and Fe and the part-bed B containing, as active material, a mixed oxide containing the elements Mo and V, in such a way that at least 96.5 mol % of propene are converted in a single pass through part-bed A.

In the gas-phase oxidation, the starting gas mixture containing propene and steam is passed at elevated temperatures (usually from about 200 to 400° C.) and atmospheric or superatmospheric pressure over transition metal mixed oxide active materials and is converted by oxidation in two steps, via acrolein, into acrylic acid (cf. for example DE-A-19 62 431, DE-A-29 43 707, DE-A-12 05 502, EP-A-0 257 565, EP-A-0 253 409, DE-A-22 51 364, EP-A-0 117 146, GB-B-1 450 986 and EP-A-0 293 224. The oxidizing agent used is oxygen.

In addition to propene, oxygen and steam, the starting gas mixture contains, as a rule, inert gases such as molecular nitrogen, CO, $CO_2$ and inert hydrocarbons. If $N_2$ is chosen as the inert diluent gas, the use of air is particularly advantageous. The molar propene/steam ratio in the starting gas mixture is $\geq 1$, preferably $\geq 1.5$, in particular $\geq 2$. In a preferred process variant, a gas mixture which is obtained from the product mixture of the gas-phase oxidation after removal of the acrylic acid by means of extraction or partial condensation is added. The propene used may be chemical grade propene (ASTM D 5273-92) which is contaminated with up to 8% of propane. A typical composition of the chemical grade propene contains at least 95% of propene and, as impurities, 3-5% of propane, ≦0.2% of C1/C2-hydrocarbon, ≦0.1% of C4-hydrocarbon, ≦10 ppm of C6-hydrocarbon, ≦0.01% of C3/C4-dienes, ≦0.01% of ethene, ≦0.005% of water, ≦1 ppm of total sulfur and ≦1 ppm of total chlorine. The propane content of the starting gas mixture of the gas-phase oxidation may not exceed 5%. The propane content is preferably ≦3%, in particular ≦2%, very particularly preferably ≦1%.

The mixed oxide active materials are converted into moldings which have a very wide range of geometries and are heaped together to form a fixed bed through which the propene-containing starting gas mixture is passed at elevated temperatures. During the contact with the mixed oxide active material, the desired oxidation occurs. If required, catalyst moldings can also be diluted with inert moldings.

The fixed catalyst bed is composed of successive catalyst part-beds A and B, the oxidation to acrolein taking place over the mixed oxide of part-bed A passed through first and the oxidation to acrylic acid taking place over the mixed oxide of part-bed B.

In the case of the catalysts, a distinction is made between various types on the basis of their preparation. If said preparation is effected by compacting pulverulent mixed oxide materials with, if required, assistants, the term unsupported catalyst is used. If the mixed oxide active material is applied to premolded inert or active catalyst supports and/or produced thereon, the term coated catalyst is used. Finally, the supported catalysts may also be mentioned, in which the mixed oxide active material is absorbed into the pores of inert supports and/or produced therein. The shaping of the mixed oxide materials or their precursors or the application thereof to supports is generally known and is described, for example, in EP-A-714 700 and EP-A-17000.

Detailed process descriptions for the preparation of catalyst moldings of mixed oxide active materials suitable according to the invention are to be found, for example, in EP-A 700 893, DE-A 10 063 162, DE-A 10 046 957, DE-A 19 948 523, EP-A 700 714, EP-A 417 723, DE-A 3300044, EP-A 552 287, EP-A 714 700, DE-A 10 059 713 and DE-A 10 051 419.

The catalyst moldings can be heaped together either as such or as a mixture with inert moldings (for example the inert supports which can be used for the preparation of coated catalysts) to give fixed catalyst beds. These fixed catalyst beds may be present, for example, in the tubes of tube-bundle reactors (cf. for example EP-A 700 893 and EP-A 700 714) or on the trays of tray reactors.

Spheres, rings and cylinders are recommended as typical geometries for the unsupported catalyst moldings, coated catalyst moldings and supported catalyst moldings for gas-phase partial oxidations.

The size of the catalyst moldings to be used according to the invention is as a rule such that the longest dimension (longest line connecting two points present on the surface of the catalyst molding) is from 2 to 12 mm, frequently from 4 to 8 mm.

Mixed oxides suitable as catalyst active material for the catalyst part-bed A are those which contain the elements Mo, Bi and Fe. Mixed oxides of the formula I $$Mo_{12}Bi_aFe_bX^1_cX^2_dX^3_eX^4_fO_n \qquad (I),$$

where $X^1$ is nickel and/or cobalt,
$X^2$ is thallium, an alkali metal and/or an alkaline earth metal,
$X^3$ is zinc, phosphorus, arsenic, boron, antimony, tin, cerium, lead and/or tungsten,
$X^4$ is silicon, aluminum, titanium and/or zirconium,
a is from 0.5 to 5,
b is from 0.01 to 5, preferably from 2 to 4,
c is from 0 to 10, preferably from 3 to 10,
d is from 0 to 2, preferably from 0.02 to 2,
e is from 0 to 8, preferably from 0 to 5,
f is from 0 to 10 and
n is a number which is determined by the valency and frequency of the elements other than oxygen in I, are preferred.

They are obtainable in a manner known per se (cf. for example DE-A 4023239, EP-A-1005908 and EP-A-575897) and can, for example, either be molded as such to give rings or spheres or used in the form of annular or spherical coated catalysts, i.e. inert supports premolded into annular or spherical form and coated with the mixed oxide active material.

In principle, suitable mixed oxide active materials I can be prepared in a simple manner by producing, from suitable sources of their elemental constituents, a very thorough, preferably finely divided dry blend having a composition corresponding to their stoichiometry and calcining said dry blend at from 350 to 650° C. The calcination can be effected both under inert gas and under an oxidizing atmosphere, e.g. air (mixture of inert gas and oxygen) and also under a reducing atmosphere (for example a mixture of inert gas, $NH_3$, CO and/or $H_2$). The duration of calcination may be from a few minutes to a few hours and usually decreases with increasing temperature. Suitable sources of the elemental constituents of the mixed oxide materials I are those compounds which are already oxides and/or those compounds which can be converted into oxides by heating, at least in the presence of oxygen.

In addition to the oxides, particularly suitable starting compounds are halides, nitrates, formates, oxalates, citrates, acetates, carbonates, amine complexes, ammonium salts and/or hydroxides (compounds, such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be decomposed during the subsequent calcination at the latest into compounds escaping completely in gaseous form, may additionally be used in the intimate dry blend).

Also advantageous for the catalyst active materials to be used in part-bed A are mixed oxides of the formula II $$[Y^1_aY^2_bO_x]_p[Y^3_cY^4_dY^5_eY^6_fY^7_gY^2_h]_q \qquad (II),$$

where $Y^1$ is bismuth, tellurium, antimony, tin and/or copper,
$Y^2$ is molybdenum and/or tungsten,
$Y^3$ is an alkali metal, thallium and/or samarium,
$Y^4$ is an alkaline earth metal, nickel, cobalt, copper, manganese, zinc, tin, cadmium and/or mercury,
$Y^5$ is iron, chromium, cerium and/or vanadium,
$Y^6$ is phosphorus, arsenic, boron and/or antimony, Y⁷ is a rare earth metal, titanium, zirconium, niobium, tantalum, rhenium, ruthenium, rhodium, silver, gold, aluminum, gallium, indium, silicon, germanium, lead, thorium and/or uranium,
a' is from 0.01 to 8,
b' is from 0.1 to 30,
c' is from 0 to 4,
d' is from 0 to 20,
e' is from 0 to 20,
f' is from 0 to 6,
g' is from 0 to 15,
h' is from 8 to 16,
x' and y' are numbers which are determined by the valency and frequency of the elements other than oxygen in II, and
p and q are numbers whose ratio p/q is from 0.1 to 10.

Mixed oxides II in which $Y^1$ is bismuth are particularly advantageous.

Preferred among these in turn are those of the formula III,

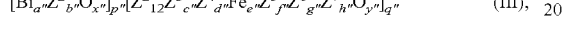

$$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \quad (III),$$

where
$Z^2$ is molybdenum and/or tungsten,
$Z^3$ is nickel and/or cobalt,
$Z^4$ is thallium, an alkali metal and/or an alkaline earth metal,
$Z^5$ is phosphorus, arsenic, boron, antimony, tin, cerium and/or lead,
$Z^6$ is silicon, aluminum, titanium and/or zirconium,
$Z^7$ is copper, silver and/or gold,
a'' is from 0.1 to 1,
b'' is from 0.2 to 2,
c'' is from 3 to 10,
d'' is from 0.02 to 2,
e'' is from 0.01 to 5, preferably from 0.1 to 3,
f'' is from 0 to 5,
g'' is from 0 to 10,
h'' is from 0 to 1,
x'' and y'' are numbers which are determined by the valency and frequency of the element other than oxygen in III, and
p'' and q'' are numbers whose ratio p''/q'' is from 0.1 to 5, preferably from 0.5 to 2, those materials III in which $Z^2_{b''}$ is (tungsten)$_{b''}$ and $Z^2_{12}$ is (molybdenum)$_{12}$ being very particularly preferred.

In a preferred embodiment, the catalyst active material of the part-bed A consists exclusively of mixed oxides which contain the elements Mo, Bi and Fe. Particularly preferably, the catalyst active material consists exclusively of mixed oxides of the formulae I, II or in particular III.

For catalyst part-bed B, mixed oxides suitable as catalyst active materials are those which contain the elements Mo and V. Mixed oxides of the formula IV

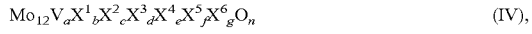

$$Mo_{12}V_aX^1_bX^2_cX^3_dX^4_eX^5_fX^6_gO_n \quad (IV),$$

where
$X^1$ is W, Nb, Ta, Cr and/or Ce,
$X^2$ is Cu, Ni, Co, Fe, Mn and/or Zn,
$X^3$ is Sb and/or Bi,
$X^4$ is one or more alkali metals,
$X^5$ is one or more alkaline earth metals,
$X^6$ is Si, Al, Ti and/or Zr,
a is from 1 to 6,
b is from 0.2 to 4,
c is from 0.5 to 18,
d is from 0 to 40,
e is from 0 to 2,
f is from 0 to 4,
g is from 0 to 40 and
n is a number which is determined by the valency and frequency of the elements other than oxygen in IV, are preferred.

Preferred embodiments within the mixed oxide active materials IV are those which are covered by the following meanings of the variables in the formula IV:
$X^1$ is W, Nb, and/or Cr,
$X^2$ is Cu, Ni, Co, and/or Fe,
$X^3$ is Sb,
$X^4$ is Na and/or K,
$X^5$ is Ca, Sr and/or Ba,
$X^6$ is Si, Al, and/or Ti,
a is from 1.5 to 5,
b is from 0.5 to 2,
c is from 0.5 to 3,
d is from 0 to 2,
e is from 0 to 0.2,
f is from 0 to 1 and
n is a number which is determined by the valency and frequency of the elements other than oxygen in IV.

However, very particularly preferred mixed oxide active materials IV are those of the formula V

$$Mo_{12}V_{a'}Y^1_{b'}Y^2_{c'}Y^5_{f'}Y^6_{g'}O_n \quad (V)$$

where
$Y^1$ is W and/or Nb,
$Y^2$ is Cu and/or Ni,
$Y^5$ is Ca and/or Sr,
$Y^6$ is Si and/or Al,
a' is from 2 to 4,
b' is from 1 to 1.5,
c' is from 1 to 3,
f' is from 0 to 0.5,
g' is from 0 to 8 and
n' is a number which is determined by the valency and frequency of the elements other than oxygen in V.

The mixed oxide active materials IV which are suitable according to the invention are obtainable in a manner known in itself, for example in a manner disclosed in DE-A 4335973, EP-A-17000 or EP-A 714700.

In principle, mixed oxide active materials of the formula IV which are suitable according to the invention can be prepared in a simple manner by producing, from suitable sources of their elemental constituents, a very thorough, preferably finely divided dry blend having a composition corresponding to their stoichiometry and calcining said dry blend at from 350 to 600° C. under inert gas, an oxidizing atmosphere, e.g. air (mixture of inert gas and oxygen) or a reducing atmosphere (e.g. a mixture of inert gas and reducing gases such as $H_2$, $NH_3$, CO, methane and/or acrolein or said reducing gases by themselves). The duration of calcination may be from a few minutes to a few hours and usually decreases with increasing temperature. Suitable sources of the elemental constituents of the mixed oxide active materials IV are those compounds which are already oxides and/or those compounds which can be converted into oxides by heating, at least in the presence of oxygen.

Advantageous ones for the catalyst active materials to be used in part-bed B are furthermore mixed oxides of the formula VI,

$$[D]_p[E]_q \quad (VI),$$

where

D is $Mo_{12}V_{a''}Z^1_{b''}Z^2_{c''}Z^3_{d''}Z^4_{e''}Z^5_{f''}Z^6_{g''}O_{x'''}$,

E is $Z^7_{12}Cu_{h''}H_{i''}O_{y'''}$, $Z^1$ is W, Nb, Ta, Cr and/or Ce,
$Z^2$ is Cu, Ni, Co, Fe, Mn and/or zn,
$Z^3$ is Sb and/or Bi,
$Z^4$ is Li, Na, K, Rb, Cs and/or H
$Z^5$ is Mg, Ca, Sr and/or Ba,
$Z^6$ is Si, Al, Ti and/or Zr,
$Z^7$ is Mo, W, V, Nb and/or Ta,
a" is from 1 to 8,
b" is from 0.2 to 5,
c" is from 0 to 23,
d" is from 0 to 50,
e" is from 0 to 2,
f" is from 0 to 5,
g" is from 0 to 50,
h" is from 4 to 30,
i" is from 0 to 20 and
x" and y" are numbers which are determined by the valency and frequency of the element other than oxygen in VI and
p and q are numbers which differ from zero and whose ratio p/q is from 160:1 to 1:1, and which are obtainable by separately preforming a multimetal oxide material E

$$Z^7_{12}Cu_{h''}H_{i''}O_{y''} \quad (E),$$

in finely divided form (starting material 1) and then incorporating, in the desired ratio p:q, the preformed solid starting material 1 into an aqueous solution, an aqueous suspension or a finely divided dry blend of sources of the elements Mo, V, $Z^1$, $Z^2$, $Z^3$, $Z^4$, $Z^5$ and $Z^6$, which contains the abovementioned elements in the stoichiometry D

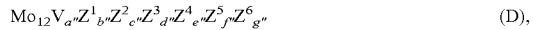
$$Mo_{12}V_{a''}Z^1_{b''}Z^2_{c''}Z^3_{d''}Z^4_{e''}Z^5_{f''}Z^6_{g''} \quad (D),$$

(starting material 2), drying any resulting aqueous mixture and calcining the dry precursor material thus obtained, before or after it is shaped into the desired catalyst geometry, at from 250 to 600° C.

Mixed oxide active materials VI in which the incorporation of the preformed solid starting material 1 into an aqueous starting material 2 is effected at ≦70° C. are preferred. A detailed description of the preparation of mixed oxide VI active materials is contained, for example, in EP-A 668104, DE-A 19736105 and DE-A 19528646.

In a preferred embodiment, the catalyst active material of part-bed B consists exclusively of mixed oxides of the formulae IV, V or preferably VI.

The novel process is preferably carried out in tube-bundle reactors coated with the catalysts, as described, for example, in EP-A 700 714 and EP-A 700 893 and in the literature cited in these publications.

In the abovementioned tube-bundle reactors, the catalyst tubes are usually produced from ferritic steel and typically have a wall thickness of from 1 to 3 mm. The internal diameter is as a rule from 20 to 30 mm, frequently from 21 to 26 mm. It is expedient in terms of application technology if the number of catalyst tubes housed in the tube-bundle container is at least 5000, preferably at least 10,000. Frequently, the number of catalyst tubes housed in the reaction container is from 15,000 to 30,000. Tube-bundle reactors having more than 40,000 catalyst tubes tend to be the exception. Within the container, the catalyst tubes are usually homogeneously distributed, the distribution expediently being chosen so that the distance between the central inner axes of adjacent catalyst tubes (the catalyst spacing) is from 35 to 45 mm (cf. for example EP-B 468 290).

Suitable heat exchange media are in particular fluid thermostating media. The use of melts of salts, such as potassium nitrate, potassium nitrite, sodium nitrite and/or sodium nitrate or of low-melting metals, such as sodium, mercury and alloys of various metals, is particularly advantageous.

Depending on the mixed oxides used, the partial oxidations are carried out at different temperatures of the catalyst part-bed. Since the reaction is an exothermic one, removal of heat is important. The temperature of the heat exchange medium and the hotspot temperature can be influenced by the reactor dimension or dilution of the catalyst.

The temperature of the heat exchange medium changes during the contact with the catalyst tubes of the tube bundle. The propene conversion or, in part-bed B, the acrolein conversion can be controlled by means of the inlet temperature (initial contact) and the quantity of energy removed, which is dependent on the flow rate and the heat capacity of the heat exchange medium. Below, the temperature of the heat exchange medium is to be understood as being the maximum temperature of the heat exchange medium over the total cooling circulation.

The hotspot temperature gives the highest hotspot value determined in the catalyst tubes. In order to determine it, for example, 5 catalyst tubes of a tube bundle which are located radially equidistant from the outside to the inside in the tube bundle are chosen and the highest value is determined.

A process in which the propene conversion is ≧97, in particular ≧97.5, particularly preferably ≧98, very particularly preferably ≧98.5, mol % in a single pass through part-bed A is preferred.

In this document, the propene conversion ($C_p$) is defined as follows:

$$C_p(mol\ \%) = \frac{\text{number of moles of propene converted}}{\text{number of moles of propene used}} \cdot 100$$

The propene conversion is determined by taking a sample at the exit of the fixed catalyst bed A for a gas chromatographic analysis.

The propene conversion can be regulated by means of the temperature of the catalyst of the part-bed A or by means of the catalyst space velocity and hence the residence time. A catalyst space velocity of at least 70 l of propene per l of catalyst per hour is preferably chosen. Catalyst space velocities above 300 are as a rule not recommended since the temperatures occurring at such high propene conversions have an adverse effect on the acrylic acid yield and moreover may influence the life of the catalyst. Catalyst space velocities of from 80 to 200 l per l per h are particularly preferably chosen in the case of mixed oxide catalysts of the formula I, preferably II, in particular III.

Characteristic magnitudes for the catalyst temperature are the temperature of the heat exchange medium and the hotspot temperature. Preferably chosen temperatures of the heat exchange medium are ≧200° C., particularly preferably from 240 to 330° C. Temperatures above 350° C. generally have an adverse effect on the life of the catalyst. These temperatures of the heat exchange medium are preferably chosen in the case of mixed oxide catalysts of the formula I, preferably II, in particular III. Hotspot temperatures in part-bed A of from 350 to 425° C., in particular from 360 to 420° C., are preferred. The pressure at which the inlet gas mixture is introduced is from 1 to 4 bar and is generally customary. The gas mixture is preferably passed into the reactor at a pressure of from 1.8 to 2.2 bar. In a preferred process variant, the pressure in the two part-beds is identical. However, it is also possible to change the pressure in part-bed B and hence the residence time by choosing a narrower or broader cross-section.

It was furthermore found that the allyl acrylate content can be influenced by the choice of the reaction conditions in part-bed B. Thus, preferred processes are those which additionally have a high acrolein conversion in the 2nd oxidation stage. It was found that processes having an acrolein conversion of ≧97 mol % and a hotspot temperature in part-bed B of ≦315° C. have a very low allyl acrylate byproduct content.

A preferred acrolein conversion after a single pass through part-bed B is ≧97, more preferably ≧97.5, particularly preferably ≧98, in particular ≧98.5, mol %.

In this document, the acrolein conversion ($C_A$) is defined as follows:

$$C_A(\text{mol \%}) = \frac{\text{number of moles of acrolein converted}}{\text{number of moles of acrolein used}} \cdot 100$$

The acrolein conversion is determined by taking a sample at the exit of the fixed catalyst bed B for a gas chromatographic analysis.

Hotspot temperatures of from 250 to 315° C., in particular from 280 to 310° C. are preferred.

The temperature of the heat exchange medium on entering the reactor is chosen in a manner known per se so that, at a given catalyst load and predetermined propene space velocity, the reaction temperature profile necessary for achieving the required acrolein conversion is established. For example, one variant comprises regulating the hotspot temperature via the energy removal. For the same residence time and hence also the same catalyst space velocity as in stage 1, this is preferably achieved at bath temperatures of the heat exchange medium of ≦250° C., preferably 245-250° C., in the total cooling circulation. As a rule, the two part-beds A and B have cooling circulations separated from one another.

The hotspot temperature can also be regulated, for example, by means of the catalyst space velocity or by dilution of the catalyst. This is done in a manner known per se.

An acrolein conversion after a single pass through part-bed B of ≧97 mol % and a maximum hotspot temperature in part-bed B of ≦315° C. for mixed oxide catalysts of the formula IV, preferably V, in particular VI, is particularly preferred.

The novel process results in a low content of troublesome byproducts. Thus, a propionic acid content of ≦400 ppm and an allyl acrylate content of ≦100 ppm are achieved therewith.

EXAMPLES 1-3

A reaction tube (V2A stainless steel, 30 mm external diameter, 2 mm wall thickness, 29 mm internal diameter, 439 cm long) was loaded from bottom to top, on a catalyst support ledge (44 cm long), first with steatite beads (from 4 to 5 mm diameter, inert material for heating the reaction gas starting mixture) having a rough surface, over a length of 30 cm, and then with the catalyst spheres prepared according to example 1 of EP-A-0 575 897 (active material of the catalyst is a mixed oxide comprising Bi, W, Mo, Fe, Co and K), over a length of 270 cm (the fixed catalyst bed A), before the loading was completed with the above-mentioned steatite beads as an after-bed over a length of 30 cm. The remaining catalyst tube length was left empty. There followed a second reaction tube (V2A stainless steel, 30 mm external diameter, 439 cm long), which was loaded with the catalyst spheres prepared according to EP-A-0 017 000 (active material of the catalyst is a mixed oxide comprising Mo, V, W and Cu), over a length of 300 cm (fixed catalyst bed B), before the loading was completed with the abovementioned steatite beads over a length of 30 cm.

Those parts of the reaction tubes which had been loaded with solid were each thermostated in a separate salt bath. Those ends of the reaction tube which were free of solid were kept at 220° C. by means of steam under superatmospheric pressure.

The reaction tube described above was continuously fed with a reaction gas starting mixture having the following composition:

6.5% by volume of propene,
3.1% by volume of $H_2O$,
0.5% by volume of Co,
1.2% by volume of $CO_2$,
0.04% by volume of acrolein,
10.7% by volume of $O_2$ and
molecular nitrogen as the remaining amount to 100% by volume.

The space velocity of the fixed catalyst bed was chosen as 100 l (S.T.P.) of propene per l per h. A small sample for a gas chromatographic analysis was taken from the product gas mixture at the exit of the fixed catalyst bed A. The temperature of the salt bath was adjusted so that the propene conversion in a single pass had the desired value in all cases. The temperatures required for this purpose are shown in the table below.

A small sample for a gas chromatographic analysis (acrolein conversion, allyl acrylate content and propionic acid content) was taken from the product gas mixture at the exit of the fixed catalyst bed B.

To ensure comparability of the experiments, the temperature of the fixed catalyst bed B was chosen so that the acrolein conversion in all cases was from 99.5 to 99.7 mol %.

The hotspot temperature was determined with the aid of a thermocouple in the reactor tube.

Table 1 below shows the dependence of the allyl acrylate content and propionic acid content on the propene conversion in mol %.

TABLE 1

| | Salt bath temperature | | Hotpoint temperature | | Propene conversion | Allyl acrylate | Propionic acid |
|---|---|---|---|---|---|---|---|
| | Stage 1 | Stage 2 | Stage 1 | Stage 2 | | | |
| Ex. 1 | 302° C. | 248° C. | 384° C. | 304° C. | 97.9% | 51 ppm | 207 ppm |
| Comp. ex. 2 | 298° C. | 250° C. | 373° C. | 317° C. | 96.1% | 104 ppm | 429 ppm |
| Comp. ex. 3 | 296° C. | 253° C. | 366° C. | 317° C. | 92.1% | 132 ppm | 623 ppm |

The selectivity S is defined as follows:

$$S(\text{mol } \%) = \frac{\text{number of moles of propene coverted into acrolein/acrylic acid}}{\text{total number of moles propene/acrolein converted}} \cdot 100$$

The novel processes have a high selectivity (>90 mol %) in combination with low byproduct contents.

EXAMPLES 4-6

Analogously to examples 1 to 3, the temperatures of the fixed catalyst bed A were chosen so that the propene conversion was from 97.7 to 97.9 mol %. Table 2 below shows the dependence of the allyl acrylate content on acrolein conversion in mol % at hotspot temperatures of from 302 to 306° C.

TABLE 2

| Ex. | Propene conversion | Salt bath temperature | | Hotpoint temperature | Acrolein conversion | Allyl acrylate |
|---|---|---|---|---|---|---|
| | | Stage 1 | Stage 2 | | | |
| 4 | 97.7% | 304° C. | 250° C. | 302° C. | 99.6% | 48 ppm |
| 5 | 97.9% | 306° C. | 247° C. | 304° C. | 98.6% | 55 ppm |
| 6 | 97.8% | 305° C. | 246° C. | 306° C. | 97.9% | 61 ppm |

We claim:

1. A process for the preparation of acrylic acid from propene by means of gas-phase oxidation, in which a starting gas mixture which contains propene and steam and whose molar propene/steam ratio is $\geq 1$ and whose propane content is $\leq 5\%$ is passed at elevated temperatures through a fixed catalyst bed comprising successive catalyst part-beds A and B, the part-bed A passed through first consisting of, as active material, at least one mixed oxide containing the elements Mo, Bi and Fe and the part-bed B consisting of, as active material, at least one mixed oxide containing the elements Mo and V, in such a way that at least 96.5 mol % of propene are converted in a single pass through part-bed A.

2. A process as claimed in claim 1, wherein the propene conversion after a single pass through part-bed A is $\geq 97.0$ mol %.

3. A process as claimed in claim 1, wherein the propene/steam ratio in the starting mixture is $\geq 1.5$.

4. A process as claimed in claim 1, wherein the catalyst space velocity is 70-300 L of propene per L of catalyst per hour.

5. A process as claimed in claim 1, wherein the active material of part-bed A is a mixed oxide of the formula $$Mo_{12}Bi_aFe_bX^1_cX^2_dX^3_eX^4_fO_n \quad (I)$$

where
- $X^1$ is nickel and/or cobalt,
- $X^2$ is thallium, an alkali metal or an alkaline earth metal,
- $X^3$ is zinc, phosphorus, arsenic, boron, antimony, tin, cerium, lead and/or tungsten,
- $X^4$ is silicon, aluminum, titanium and/or zirconium,
- a is from 0.5 to 5,
- b is from 0.01 to 5,
- c is from 0 to 10,
- d is from 0 to 2,
- e is from 0 to 8,
- f is from 0 to 10 and
- n is a number which is determined by the valency and frequency of the elements other than oxygen in I.

6. A process as claimed in claim 1, wherein the active material of the part-bed B is a mixed oxide of the formula IV $$Mo_{12}V_aX^1_bX^2_cX^3_dX^4_eX^5_fX^6_gO_n \quad (IV)$$

where
- $X^1$ is W, Nb, Ta, Cr and/or Ce,
- $X^2$ is Cu, Ni, Co, Fe, Mn and/or Zn,
- $X^3$ is Sb and/or Bi,
- $X^4$ is one or more alkali metals,
- $X^5$ is one or more alkaline earth metals,
- $X^6$ is Si, Al, Ti and/or Zr,
- a is from 1 to 6,
- b is from 0.2 to 4,
- c is from 0.5 to 18,
- d is from 0 to 40,
- e is from 0 to 2,
- f is from 0 to 4,
- g is from 0 to 4 and
- n is a number which is determined by the valency and frequency of the elements other than oxygen in IV.

7. A process as claimed in claim 1, further comprising:
condensing the acrylic acid from a gas mixture;
esterifying the acrylic acid; and
polymerizing the acrylic acid.

8. A process as claimed in claim 1, wherein the process produces an acrylic acid composition that contains less than 400 ppm of propionic acid and less than 100 ppm of allyl acrylate without additional aftertreatment steps.

* * * * *